United States Patent [19]

Stepke et al.

[11] Patent Number: 4,521,119
[45] Date of Patent: Jun. 4, 1985

[54] CONSTANT LOAD DILATOMETERS

[75] Inventors: Anthony C. Stepke, New Hyde Park; Gerhard R. Clusener, Manhasset, both of N.Y.

[73] Assignee: Theta Industries, Inc., Port Washington, N.Y.

[21] Appl. No.: 538,180

[22] Filed: Oct. 3, 1983

[51] Int. Cl.³ ............................................ G01N 25/16
[52] U.S. Cl. ........................................ 374/56; 336/30; 336/136
[58] Field of Search ...................... 374/6, 7, 55, 56, 57; 336/30, 136; 33/147 D, 148 D

[56] References Cited

U.S. PATENT DOCUMENTS

3,680,357 8/1972 Clusener .............................. 374/56
3,748,892 7/1973 McKendree, Jr. et al. .......... 374/56

Primary Examiner—Charles Frankfort
Assistant Examiner—Thomas B. Will
Attorney, Agent, or Firm—Burton E. Levin

[57] ABSTRACT

Differential dilatometers are described which employ a linear variable differential transformer dilation sensor in which the core and/or coil is independently supported to accommodate the imposition of a constant load on a specimen abutting a pushrod coupled to that transformer element. The independent support system has at least one collar that slidably enages a mating extension of the supported transformer element, thereby permitting long range axial movement of that element while rigidly restricting lateral movement. The collar which thus holds the supported transformer element may be tilted by an adjustable clamp on at least one plant parallel to the path of axial movement of that element, thereby facilitating alignment adjustment. In a specifically illustrated independent support system of this type, the supported transformer element bears two such extensions, each of which slidably engages a separate collar containing linear ball bearings, the collars are held in firm alignment by a yoke and the yoke is held by an adjustable clamp that permits the supported element to be tilted on two perpendicualr planes, both of which are parallel to its path of axial movement.

20 Claims, 9 Drawing Figures

CONSTANT LOAD DILATOMETERS

BACKGROUND OF THE INVENTION

1. Field of the Invention

This invention relates generally to dilatometers and, more particularly, to dilatometers having a linear variable differential transformer dilation sensor with an improved independent support mechanism for the core or coil or both which permits the maintenance of a constant load on the test specimen and facilitates accurate measurements on a specimen which is subject to large dimensional changes with changes in temperature.

2. Description of the Prior Art

Dilatometers are analytical instruments that respond to the linear thermal expansion or contraction of solids. Typically, these instruments have a variable temperature furnace in which the test specimen rests between a flat surface on a stationary object and an opposing flat surface on a movable object, such as a ceramic pushrod, that extends outside the furnace. Temperature induced changes in the length of the specimen are transmitted through the rod to a mechanical, optical or electrical system for amplifying and measuring that change. These instruments can be used to make precise measurements of changes in length resulting from small temperature changes or to plot variations in the rate of linear expansion or contraction over a broad temperature range.

U.S. Pat. Nos. 3,680,357 and 3,898,836 describe a particularly accurate type of dilatometer in which the dilation sensor is a linear variable differential transformer in which the core floats freely in the coil and each of these elements is separately supported at its ends by a pair of compound cantilevered springs. These springs permit independent and frictionless axial movement of the suspended element, but restrain radial or transverse movement. This independent and frictionless axial movement of the core and coil facilitates calibration of the linear variable transformer and, when core and coil are coupled to separate pushrods, it makes possible exceptionally accurate differential measurements of two different specimen materials.

Such differential measurements are invaluable in studying the compatibility under changing temperature conditions of different materials which are bonded together or are in close contact; e.g., metal to glass, enamel to substrates, thin film deposits in microcircuits or metal or plastic fillings in natural teeth. When the coil and core pushrods are of the same material and configuration and they extend the same distance into the furnace, the linear variable differential transformer automatically compensates for dilation of those pushrods. Two pushrod dilatometers of this type also are useful for making measurements on a single specimen. When one pushrod abuts the specimen and the other abuts the fixed specimen support adjacent the specimen, the dilation of the fixed support likewise is cancelled by the linear variable differential transformer.

The ability of a dilatometer to compensate automatically for pushrod and fixed specimen support dilation is especially important in applications where a massive fixed specimen support is essential or large specimen dilation necessitates the use of unusually long pushrods which extend deeply into the furnace. Exemplary of such applications is the use of a two rod dilatometer in simulating commercial processes, such as firing of ceramics or sintering of either metallic or non-metallic powders, and in determining the softening point of glass by parallel plate viscometry.

In simulating the firing of ceramics or the sintering of powders, one pushrod typically abuts the fixed specimen support and the element of the linear variable differential transformer to which that pushrod is coupled is subjected to relatively small axial displacement. The other element, however, is coupled to the pushrod that abuts a specimen that shrinks significantly under the influence of heat and this element is subjected to much greater axial displacement. While the requirement for this large axial displacement (i.e., long range) can be accommodated by supporting that element on larger than normal compound cantilevered springs, such large springs add undesirable mass to the dilatometer measuring head and often may impose an undesirably large load on the specimen.

In order to overcome these shortcomings, a two pushrod dilatometer has been developed in which a short range coil of the horizontally oriented linear variable differential transformer is supported by a pair of conventional compound cantilevered springs, and a long range core is provided by supporting that core on linear ball bearings within tubular housings that are welded to the ends of the coil and that encircle the protruding ends of the core. A small constant load on the specimen is provided by a weight attached to a cord that passes over a pulley and connects to the core, thereby urging the core and its pushrod toward the specimen.

While this two pushrod dilatometer design provided the long range and small constant specimen loading that are desirable for handling specimens that shrink significantly, accurate alignment of both elements of the linear variable differential transformer and their coupled pushrods with the specimen and fixed specimen support proved to be an exceedingly tedious operation. This was due to the fact that the core and coil were laterally locked together and the weight of both, as well as that of both pushrods, was carried by the pair of springs attached to the coil.

Lateral movement of the coil for alignment purposes could be accomplished by making small adjustments in the points of attachment of the single pair of springs to the dilatometer base (as was commonly done with dilatometers having two pairs of springs), but it was an awkward operation because of the necessity of manually holding the entire unwieldy assembly of coil, coil springs, core and two pushrods in proper position while changing the points of spring attachment and securing those springs to the dilatometer base. Independent lateral movement of the core was not possible.

In addition, the laterally locked together coil and core necessitated an unusual degree of precision in alignment, particularly when it was desirable to impose a large constant load on the specimen through the long range core. Unless the core, its coupled pushrod and the specimen were accurately aligned, the lateral vector of a heavy loading force might exceed the capacity of the single pair of springs to limit lateral displacement of the entire assembly of core, coil and two pushrods.

SUMMARY OF THE INVENTION

It is an object of this invention to provide an improved dilatometer for measuring large changes in the linear dimension of a solid specimen. A further object of the invention is to provide such dilatometer employing, as the dilation sensor, a linear variable differential transformer in which the core and coil are independently supported and each is attached to a separate pushrod to facilitate differential measurements. It is a specific object of this invention to provide an improved means of support for the coil or core or both which will accommodate long range axial movement of the supported member while rigidly restricting lateral movement, but which will permit the operator to make independent adjustments in the lateral position of the supported member for alignment purposes, as well as to apply a desired constant load to the specimen.

It has been found that these objects and other advantages, which will be apparent from this specification, are achieved by the invention described below.

One aspect of my invention is apparatus for independently supporting and adjusting the alignment of the coil or core of a linear variable differential transformer comprising (a) a collar which is adapted to slidably engage an elongated extension of said supported member to permit linear movement thereof on its longitudinal axis and (b) adjustable clamping means coupled to said collar for holding and tilting said collar and said supported member on at least one plane parallel to said longitudinal axis.

When the supported member is the core of the linear variable differential transformer, one may employ a single longitudinally elongated collar which engages a coaxially positioned mating extension of the core which protrudes from either end of the coil. Such single collar is coupled to a first adjustable clamp for tilting the collar and core on a first plane parallel to the longitudinal axis of the core. Desirably, this first adjustable clamp engages a second adjustable clamp for tilting the first adjustable clamp, the collar and the core on a second plane parallel to the longitudinal axis of the core. For most applications these planes advantageously are about 90° apart.

It is preferred however, to employ a pair of tubular collars, advantageously containing linear ball bearings within round bores, each of which encircles and slidably engages one of a pair of round rod shaped extensions that are coaxially positioned on opposite ends of the core and which protrude from the coil. It likewise is preferred that this pair of collars be held in firm coaxial alignment by a yoke that bypasses the coil, such yoke being held by the first adjustable clamp and being lockably rotatable thereon on a plane parallel to the longitudinal axis of the core. Rotation of the yoke tilts both of the collars and the core on that plane. This first adjustable clamp advantageously is held by the second adjustable clamp on which it is lockably rotatable on a second plane parallel to the longitudinal axis of the core. Rotation of the first adjustable clamp rotates the yoke and tilts both of the collars and the core on that second plane. As in the case of the single collar support system, it usually is desirable that these planes be about 90° apart.

When the supported element is the coil of the linear variable differential transformer, one likewise may employ a single longitudinally elongated collar which is similar to the single collar described above for supporting the core, but which differs in that it engages a mating extension of the coil that is positioned parallel to the longitudinal axis of the coil and spaced apart from its outer wall. Since it usually is desirable to prevent rotation of the coil about its longitudinal axis, such single collar advantageously has an asymmetric orifice.

It is, however, preferred to employ a pair of tubular collars having linear ball bearings within round bores, which, in contrast to the pair of collars of the core support system, are held in firm parallel alignment by a yoke. Each of these collars encircles and slidably engages a separate round rod extension of the coil which is positioned parallel to both the longitudinal axis of the coil and the other rod and is spaced apart from both the outer wall of the coil and the other rod.

Adjustment of the alignment of a coil held by such single or dual collar support systems is accomplished with adjustable clamps in the same manner as the single and dual collar core support systems described above.

A second aspect of this invention is a constant load dilatometer comprising (a) a linear variable differential transformer dilation sensor having a core member freely floating in a coil member, at least one of said core and coil members being axially movable, being coupled to a pushrod that is adapted to abut a specimen held between said pushrod and a stationary object in a furnace and being independently supported for application of a constant load to said specimen, said supported member bearing a straight elongated extension that is parallel to its path of axial movement, (b) adjustable support apparatus which permits long range axial movement and alignment adjustment of said supported member while rigidly restricting transverse movement thereof, said support apparatus comprising (i) a collar which slidably engages said extension and (ii) adjustable clamping means coupled to said collar for holding and tilting said collar and said supported member on at least one plane parallel to the longitudinal axis of said member and (c) means for varying the force applied to said specimen by said pushrod.

A preferred embodiment of such constant load dilatometer is a differential dilatometer in which both of the coil and core members are capable of independent axial movement, each is coupled to a separate pushrod and at least one is supported by adjustable support apparatus, as described above, which includes a pair of collars bridged by a yoke that is lockably rotatable on at least one plane parallel to the longitudinal axis of the supported member. It also is preferred, for precise control of alignment, that the differential dilatometer employ such adjustable support apparatus which permits rotation of the yoke and tilting of the supported member on two planes parallel to its longitudinal axis.

DESCRIPTION OF THE PREFERRED EMBODIMENTS

The preferred embodiment of this invention illustrated by FIGS. 1 through 6 is a differential dilatometer in which both the core and coil of the linear variable differential transformer dilation sensor are supported for independent long range axial movement, alignment adjustment and constant specimen loading. It is especially well suited for handling specimens which exhibit large temperature induced dimensional changes. A typical application of such dilatometer is to compare the behavior of two different metal powders under sintering conditions.

This dilatometer has a horizontal base plate 1 supporting a vertical post 2 which has a longitudinal groove 2a. A clamping bracket 3 slidingly engages post 2 and is rotationally restrained by finger 3a which extends into groove 2a, as shown most clearly in FIG. 5. Bracket 3 is locked at a desired position on post 2 by depressing lever 3b. A carriage 4, having an indentation 4a in its edge, is firmly secured to bracket 3 and indirectly supports the independently movable and adjustable core 6 and coil 14 of the linear variable differential transformer dilation sensor.

Core 6 floats freely within coil 14 and has round rod extensions 7 which protrude from opposite ends of coil 14. Each of these extensions 7 slidably engages linear ball bearings (shown only in the alternate embodiment illustrated in FIG. 9) held within a tubular collar 8 which encircles that core extension. Collars 8 are held in firm coaxial alignment by C-shaped yoke 10 that bypasses coil 14 and is adjustably attached to carriage 4 through first clamping screw 11, block 12 and second clamping screw 13. Single plane alignment adjustment is made possible by screw 11, which is threaded into yoke 10, and block 12, which is journaled for rotation of a loosened screw 11. Yoke 10 and loosened screw 11 can be rotated on a first plane parallel to the longitudinal axis of core 6, thereby tilting collars 8 and core 6 on that first plane. The entire assembly of yoke 10, collars 8 and core 6 then can be locked to block 12 in a desired position by tightening screw 11.

Alignment adjustment on a second plane is made possible by second clamping screw 13 which passes through block 12 perpendicular to screw 11 and is threaded into carriage 4. Block 12, which is journaled for rotation on a loosened screw 13, and yoke 10 can be rotated on a second plane parallel to the longitudinal axis of the core 6 and normal to the first plane, thereby tilting collars 8 and core 6 on that second plane. The entire assembly of block 12, yoke 10, collars 8 and core 6 then can be locked in a desired position by tightening screw 13 into carriage 4.

The upper end of coil 14 passes through an opening 15b in first plate 15 and is held firmly by screw 15c which, when turned in, narrows opening 15b. The lower end of coil 14 is similarly held by second plate 16, which has an opening 16b and a narrowing screw 16c. First rod 17 and second rod 18, which are parallel to coil 14, also are attached at their ends to plates 15 and 16. Each of rods 17 and 18 slidably engages linear ball bearings (not shown) held within a tubular collar 19 which encircles that rod. Collars 19 are held in firm parallel alignment by L-shaped yoke 21 that is spaced apart from coil 14 and is adjustably mounted on carriage 4 through third clamping screw 22, block 23 and fourth clamping screw 24. Single plane alignment adjustment is made possible by screw 22, which is threaded into block 23, and yoke 21, which is journaled for rotation on a loosened screw 22. Rotation of yoke 21 on a first plane parallel to the longitudinal axis of coil 14 tilts the entire assembly of collars 19, plates 15 and 16, rods 17 and 18 and coil 14 on that first plane. By tightening screw 22, the assembly can be locked to block 23 in a desired position.

Alignment adjustment on a second plane is made possible by fourth clamping screw 24, which passes through block 23 perpendicular to screw 22 and is threaded into the edge of carriage 4 at indentation 4a. Block 23, which fits loosely in indentation 4a and is journaled for rotation on a loosened screw 24, and yoke 21 can be rotated on a second plane parallel to the longitudinal axis of coil 14 and normal to the first plane, thereby tilting the entire assembly of collars 19, plates 15 and 16, rods 17 and 18 and coil 14 on that second plane. By tightening screw 24, the assembly can be locked to carriage 4 in a desired position.

Calibration of the linear variable differential transformer is accomplished with micrometer head 27 which is held by bracket 28 extending from carriage 4 and which can be turned in to bear on an anvil 15a attached to the top of first plate 15. By so doing, coil 14 is displaced relative to core 6 by an accurately measured distance and the electrical output of the linear variable differential transformer corresponding to that displacement can be precisely recorded. While making measurements on specimens, the micrometer must, of course, be backed off to permit the coil to move freely.

Figure 2:
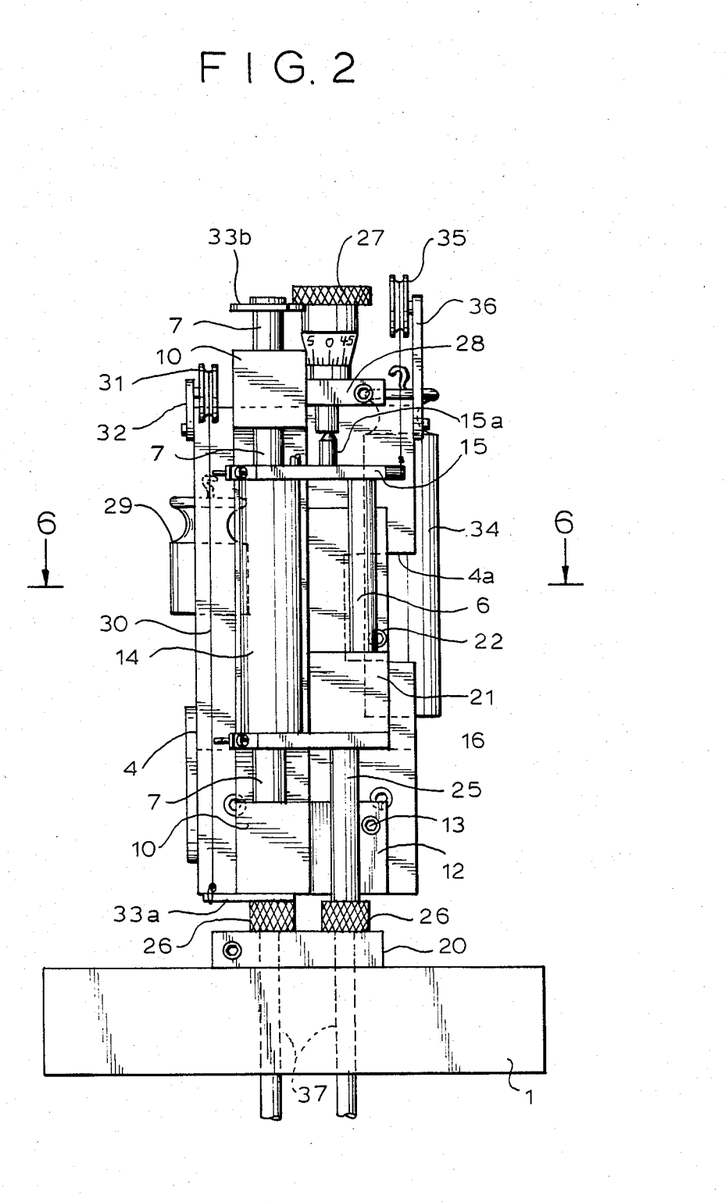
FIG. 2 is a front elevation of the dilatometer of FIG. 1.
Figure 3:
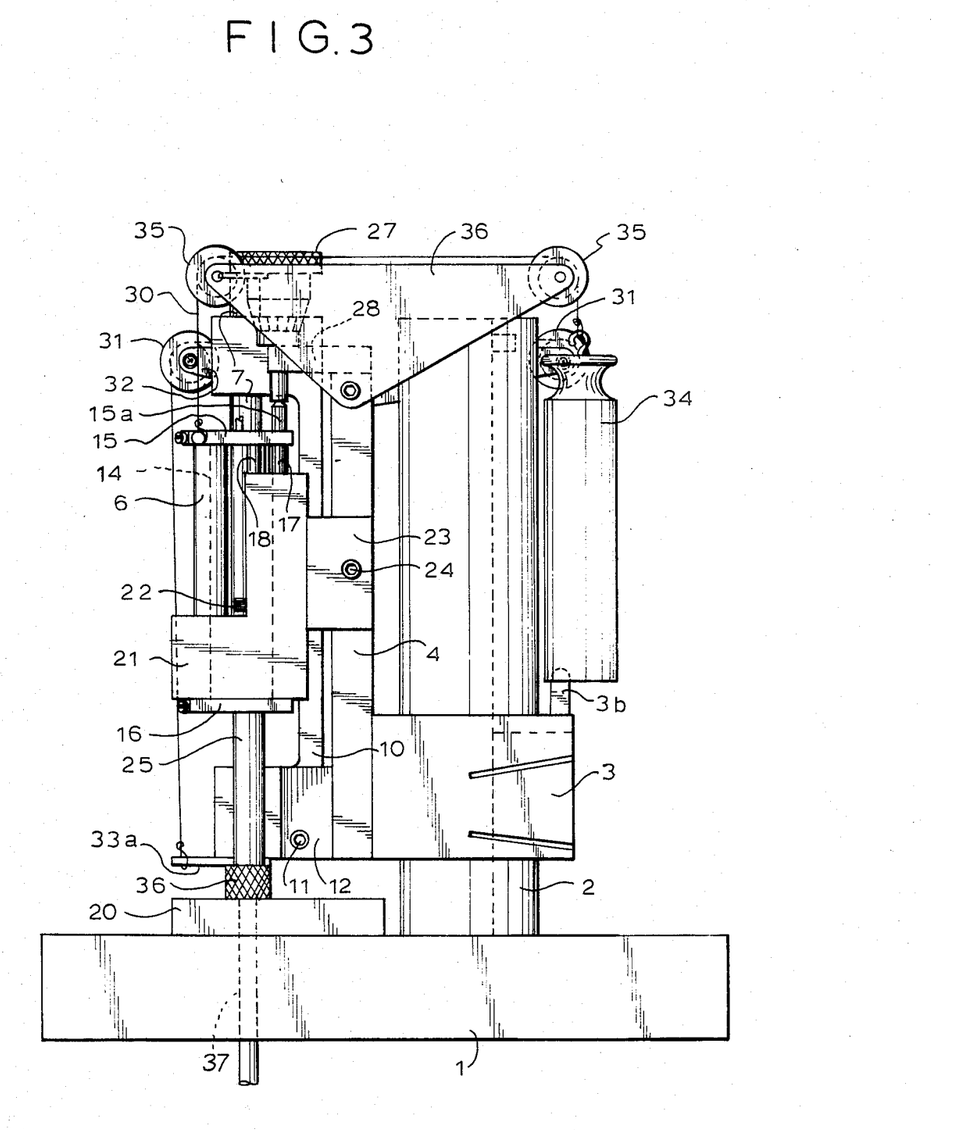
FIG. 3 is a right side elevation of the dilatometer of FIG. 1.
Figure 4:
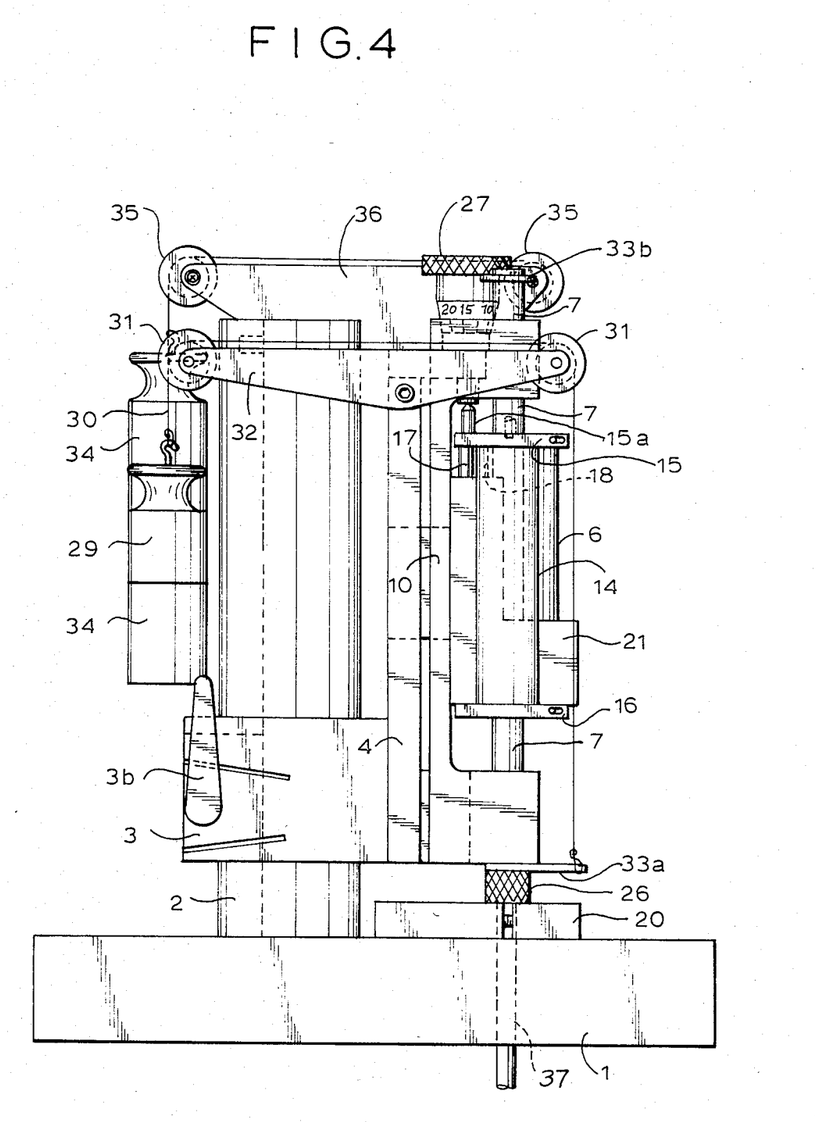
FIG. 4 is a left side elevation of the dilatometer of FIG. 1.
Figure 5:
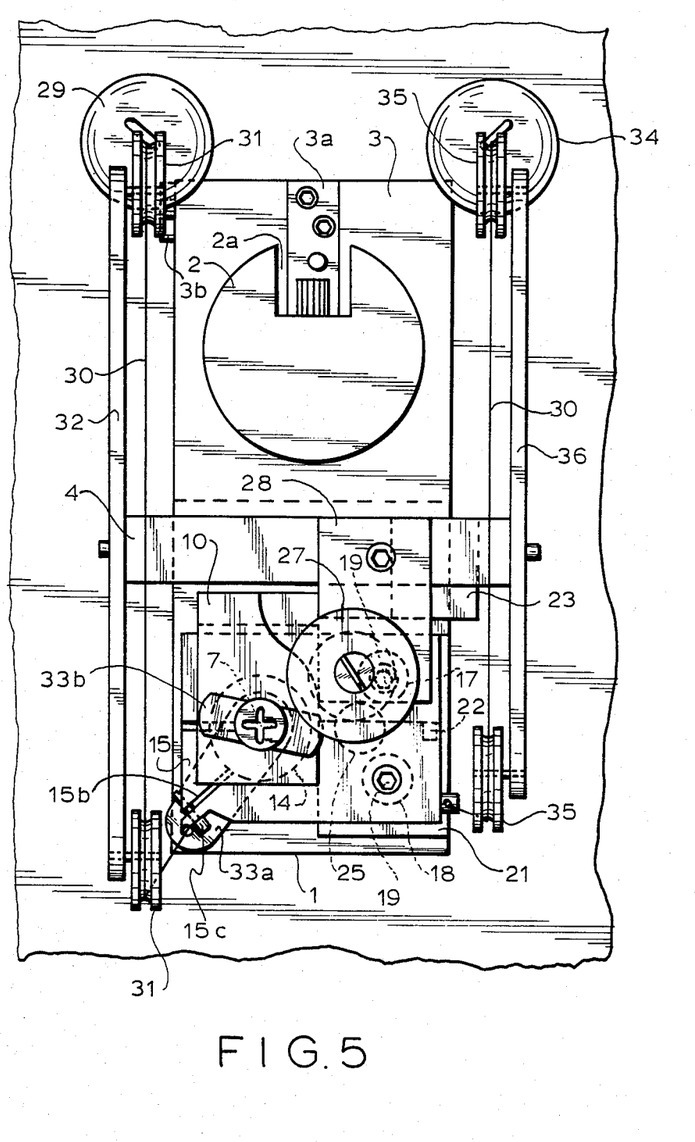
FIG. 5 is a top plan view of the dilatometer of FIG. 1.
Figure 6:
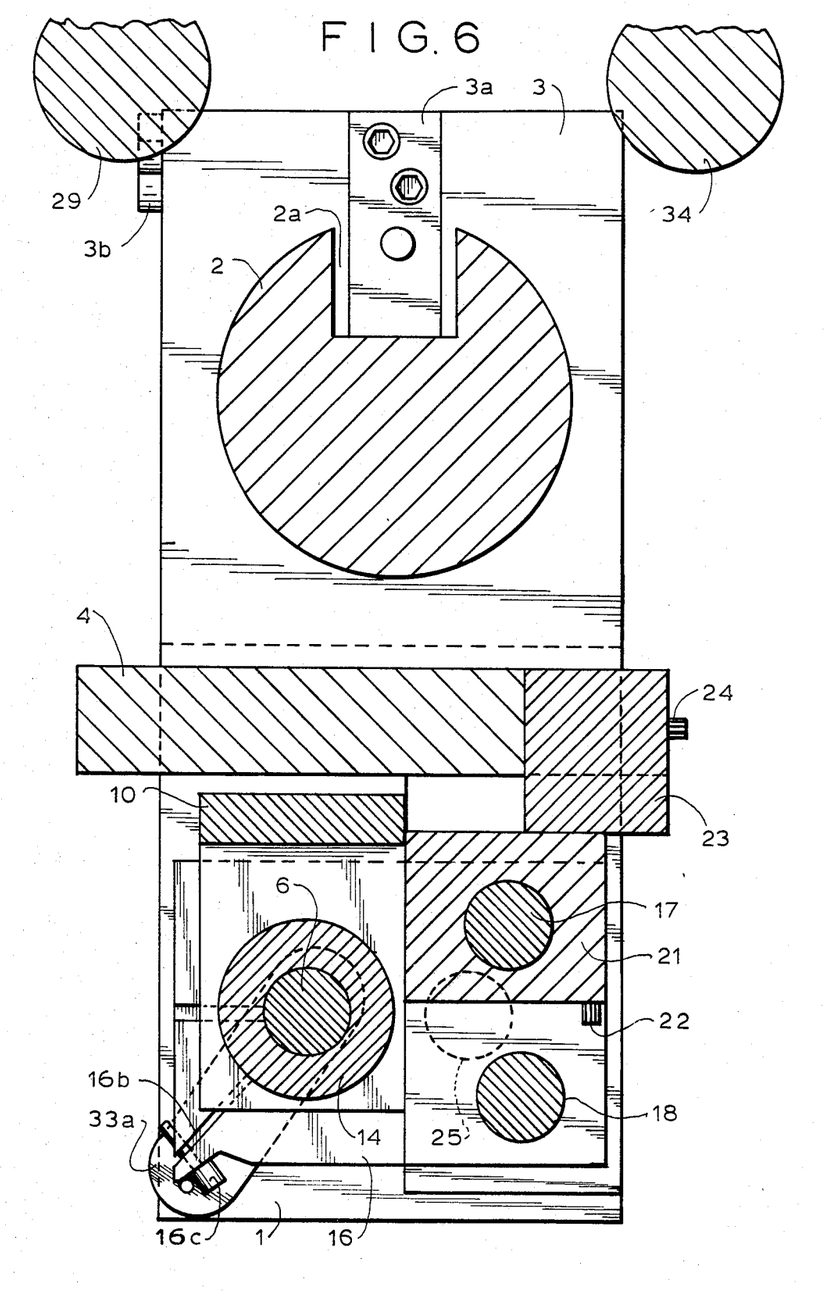
FIG. 6 is cross section of the dilatometer of the dilatometer of the preceding figures taken along plane 6—6.

As shown most clearly in FIG. 2, lower core extension 7 and coil extension 25 each terminates in a pushrod clamp 26 which holds a pushrod 37. Each of these pushrods 37 passes loosely through a hole in temperature stabilized block 20 (internal passageways for cooling water not shown) and base plate 1 to abut a specimen (not shown) that is held, in a conventional manner, between the flat end of that pushrod and a flat surface on a stationary object within a furnace (neither shown).

A constant load, which is less than the total weight of the core 6, core extensions 7 and the attached pushrod clamp 26 and pushrod 37, can be imposed on a core specimen by means of weight 29 which is attached to one end of a string 30 that passes over pulleys 31 and also is attached to first flange 33a on lower core extension 7. Pulleys 31 are carried at opposite ends of beam 32 which is fastened to an upper edge of carriage 4. By adjusting the weight of weight 29, the upward force applied to the core can be varied and a constant load of one gram or less can be achieved readily. This ability to apply a small constant load is particularly important when making measurements on easily deformed specimens, such as metal powders or heat softened glass. A reduced constant load similarly can be imposed on the coil specimen by weight 34 which is attached, by means of a string 30 passing over pulleys 35, to upper plate 15.

Pulleys 35 are carried at opposite ends of beam 36 which is fastened to a upper edge of carriage 4.

When an increased constant load on a core specimen is required, as for example in parallel plate viscometry, the weight 29 causing the upward force on the pushrod abutting that specimen desirably is removed and an additional weight (not shown) can be imposed on flange 33b at the upper end of upper core extension 7. Similarly, an increased constant load on a coil specimen requires disconnecting weight 34 and the addition of a weight (not shown) to the top of upper plate 15.

Figure 7:
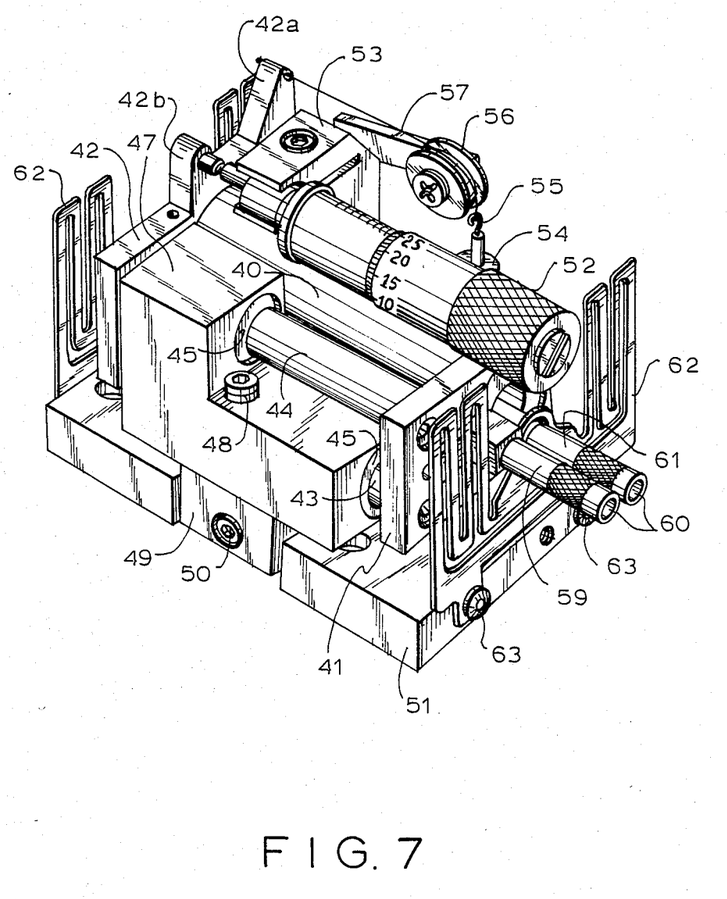
FIG. 7 is a perspective view of another dilatometer embodiment of this invention showing adjustable support apparatus for the coil of a horizontally oriented linear variable differential transformer dilation sensor, the core being supported by a conventional compound cantilevered spring.

FIG. 7 illustrates another dilatometer of this invention in which the linear variable differential transformer dilation sensor is horizontally oriented and only one of the transformer elements, the coil, is supported for long range movement and constant loading by an adjustable support system that is substantially the same as that used for the coil in the previously described embodiment. The core is conventionally supported for shorter range movement. This illustrated dilatometer is particularly useful for measuring the shrinkage of a green ceramic specimen in a furnace that is programmed to simulate commercial firing. Since a typical green ceramic specimen is large, easily deformed and shrinks substantially during firing, it advantageously is abutted by a lightly loaded pushrod coupled to the long range coil. Because it is large, it must be held, during dilation measurement, against a flat surface on a large stationary object within the furnace. In contrast to the green ceramic specimen, such stationary object generally expands slightly during heating and coil movement reflects the cumulative dilation of the two materials. The influence of the stationary object expansion on the electric output of the linear variable differential transformer is, however, cancelled by the core pushrod which abuts the flat surface of the stationary object adjacent to the point of contact of the specimen. Core movement is responsive only to expansion of the stationary object which, in effect, is employed as a second or reference specimen in a differential measurement.

Coil 40 is attached at one end to plate 41 and at the other end to plate 42. Rods 43 and 44, which are parallel to the longitudinal axis of coil 40 are attached at their ends to plates 41 and 42. Each rod is slidably encircled by a tubular collar 45 having linear ball bearings (shown only in the alternate embodiment illustrated in FIG. 8) at its inner surface. Collars 45 are held in firm parallel alignment by an L-shaped yoke 47 which is adjustably mounted on base plate 51 by means of a first clamping screw 48, which passes through yoke 47 and is threaded into block 49, and second clamping screw 50, which passes through block 49 and is threaded into base plate 51. Two plane adjustment of the coil position is accomplished in the same manner as in the previously described embodiment; i.e., by loosening the clamping screws, rotating the assemblies held by those screws and then tightening the screws.

The freely floating core (not visible) has an extension 61 at each end that protrudes from the coil 40 and is held by a conventional compound cantilevered spring 62 mounted on base plate 51. Small adjustments in the position of springs 62 and the core can be made by loosening screws 63 which pass loosely through relatively large openings in the bottom of springs 62 and are threaded into base plate 51.

A coil extension 59 is attached at one end to plate 41. Coil extension 59 and adjacent core extension 61 each bears a pushrod clamp 60 holding a ceramic pushrod (not shown) which abuts a specimen in a furnace (neither shown). A predetermined constant load can be imposed on the coil pushrod by adjusting the weight 54 attached to one end of the string 55 which passes over pulley 56 and is attached to lip 42a on plate 42. Pulley 56 rotates on an arm 57 of bracket 53 which is attached to base plate 51.

Bracket 53 also supports micrometer head 52 which can be brought to bear on lip 42b of second plate 42 to displace the coil relative to the core a measured distance for calibration purposes, as in the preceding embodiment.

The embodiment of FIG. 7 can, of course be modified to provide a long range constant load support for the core. In such modification, the core advantageously is supported by a pair of tubular collars held by a C-shaped yoke, as in FIGS. 1-6. When the core is so supported, the coil can be supported as shown in FIG. 7 or it may be supported at its ends by a pair of conventional compound cantilevered springs when long range and constant loading is not a requirement. The embodiment of FIGS. 1-6 similarly can be modified by employing such conventional spring support for either the core or coil.

The adjustable clamping means illustrated in FIGS. 1-7 for supporting and aligning a linear variable differential transformer element also can be modified easily. Alternate and especially preferred embodiments of this aspect of the invention are shown in FIGS. 8 and 9, which can be substituted for functionally equivalent structures in FIGS. 7 and 1, respectively.

Figure 8:
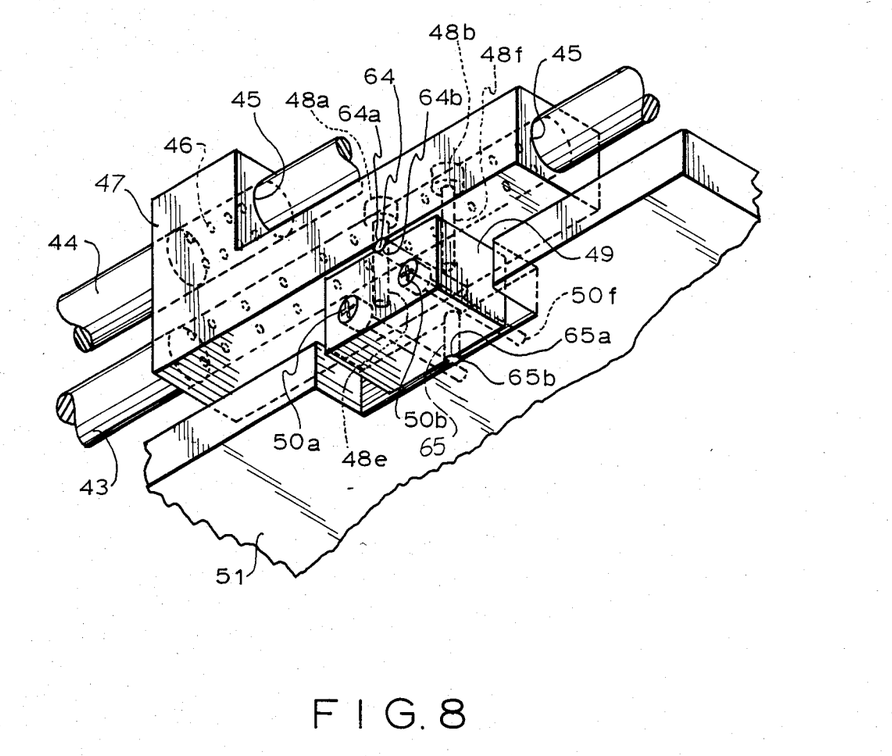
FIG. 8 is a perspective view of an alternate form of adjustable support apparatus for the linear variable differential transformer coil of the dilatometer of FIG. 7.

In FIG. 8, as in FIG. 7, parallel extension rods 43 and 44 of the coil (not shown) are slidably held by linear ball bearings 46 within collars 45 that are firmly joined by L-shaped yoke 47. Yoke 47 rests on dowel pin 64 which can turn in matching shallow depressions 64a and 64b on yoke 47 and rectangular block 49. Screws 48a and 48b pass loosely through yoke 47 on opposite sides of dowel pin 64 and are threaded into block 49 to hold yoke 47 on dowel pin 64. When both screws 48a and 48b are loose, yoke 47 can be rocked on dowel pin 64, thereby tilting the coil on a first plane parallel to its longitudinal axis. By loosening one of the screws and tightening the other, yoke 47 and the coil can be adjustably positioned with great precision.

Block 49 also rests on a dowel pin 65 which is perpendicular to dowel pin 64 and which can turn in matching shallow depressions 65a and 65b on block 49 and base 51. This depression on block 49 is on a face that is perpendicular to that abutting dowel pin 64. Screws 50a and 50b pass loosely through block 49 on opposite sides of dowel pin 65 and are threaded into base 51 to hold block 49 on dowel pin 65. By loosening one of these screws and tightening the other, block 49 can be rocked on dowel pin 65, thereby tilting the coil on a second plane which is parallel to its longitudinal axis and perpendicular to the first plane of rotation.

Figure 1:
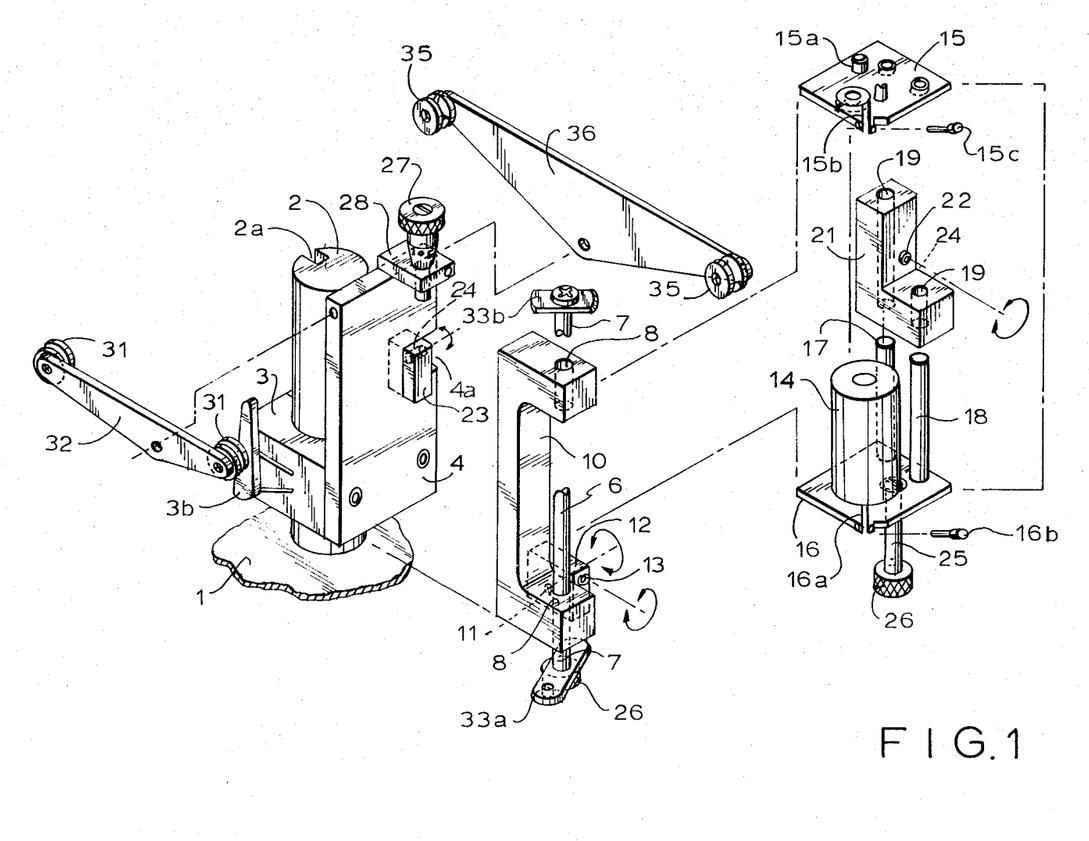
FIG. 1 is an exploded perspective view, with sections and elements omitted for clarity, of a dilatometer embodiment of this invention showing separate adjustable support apparatus for both the core and coil of a vertically oriented linear variable differential transformer dilation sensor.
Figure 9:
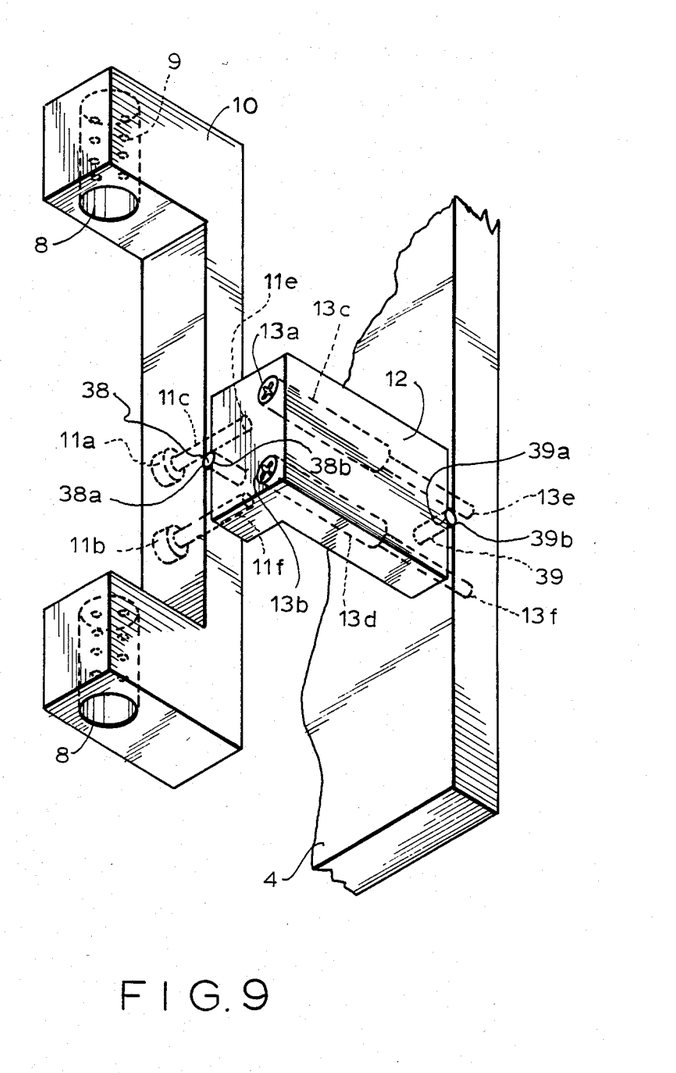
FIG. 9 is a perspective view of an alternate form of adjustable support apparatus for the linear variable differential transformer core of the dilatometer of FIG. 1.

In FIG. 9, as in FIG. 1, the extension rods of the linear variable differential transformer core (neither shown) rest on linear ball bearings 9 within collars 8 that are held in firm coaxial alignment by C-shaped yoke 10. Yoke 10 rests on dowel pin 38 which can turn in matching shallow depressions 38a and 38b in yoke 10 and block 12. Screws 11a and 11b pass loosely through yoke 10 on opposite sides of dowel pin 38. Block 12 also rests on dowel pin 39, which is perpendicular to pin 38 and which can turn in matching shallow depressions 39a and 39b on another face of block 12 and on carriage 4. Screws 13a and 13b pass loosely through block 12 on opposite sides of dowel pin 39 and are threaded into carriage 4. Tilting of the core on two perpendicular planes, both of which are parallel to its longitudinal axis, can be accomplished by adjusting screws 11a, 11b, 13a and 13b in the same manner as described above with respect to the coil of FIG. 8.

A major advantage of the embodiments illustrated by FIGS. 8 and 9 is that one can, by loosening a screw on one side of a dowel pin and simultaneously tightening the screw on the other side, maintain a firm mechanical grip on the supported structure at all times, thereby facilitating continuously variable alignment adjustments without the necessity of manually holding or moving that structure.

It will, of course, be understood that various other modifications and additions may be made in the embodiments of this invention described above without departing from the spirit and scope of the invention as defined in the claims below.

We claim:

1. Apparatus for independently supporting and adjusting the alignment of a member selected from the coil and core of a linear variable differential transformer comprising
   (a) a collar which is adapted to slidably engage an elongated extension of said selected member to permit linear movemnt thereof on its longitudinal axis and
   (b) adjustable clamping means coupled to said collar for holding and tilting said collar and said selected member on at least one plane parallel to said axis.

2. Apparatus of claim 1 including a second collar which is adapted to slidably engage a second elongated extension of said selected member to permit linear movement thereof on its longitudinal axis, said collars being held in firm alignment by a yoke which is held by said adjustable clamping means and which is lockably rotatable thereon on a plane parallel to the longitudinal axis of said selected member.

3. Apparatus of claim 2 wherein said selected member is the core of a linear variable differential transformer, said extensions extend coaxially from opposite ends of said core and said collars are held in firm coaxial alignment by said yoke.

4. Apparatus of claim 2 wherein said selected member is the coil of a linear variable differential transformer, each of said extensions is positioned parallel to the longitudinal axis of said coil and is spaced apart from said coil and the other said extension and said collars are held in firm parallel alignment by said yoke.

5. Apparatus of claim 2 wherein said adjustable clamping means comprises a clamping block, a pivot held intermediate said block and said yoke, said yoke being rotatable on a plane parallel to the longitudinal axis of said selected member, and means for locking said yoke to said clamping block.

6. Apparatus of claim 5 wherein said pivot is a shaft on which said yoke is rotatable and said yoke is rotationally locked by a fastener connecting said yoke to said clamping block.

7. Apparatus of claim 6 wherein said yoke is journaled for rotation on said shaft and said shaft is threaded into said clamping block to firmly connect said yoke to said clamping block and to lock said rotation.

8. Apparatus of claim 6 wherein said clamping block is journaled for rotation of said shaft and said shaft is threaded into said yoke to firmly connect said yoke to said clamping block and to lock said rotation.

9. Apparatus of claim 5 wherein said pivot is a dowel pin on which said yoke is rotatable and said yoke is rotationally locked by fasteners which are positioned on opposite sides of said dowel pin and which connect said yoke to said clamping block.

10. Apparatus of claim 5 wherein said adjustable clamping means is attached to a second adjustable clamping means to render said yoke lockably rotatable on two perpendicular planes, both of which are parallel to the longitudinal axis of said selected member, said second adjustable clamping means comprising a fixed clamping block, a second pivot held intermediate said clamping block and said fixed clamping block, said clamping block being lockably rotatable on a plane normal to the plane of rotation of said yoke, and means for locking said clamping block to said fixed clamping block.

11. Apparatus of claim 10 wherein said second pivot is a shaft on which said clamping block is rotatable and said clamping block is rotationally locked by a fastener connecting said clamping block to said fixed clamping block.

12. Apparatus of claim 11 wherein said clamping block is journaled for rotation on said shaft and said shaft is threaded into said fixed clamping block to firmly connect said clamping block and said fixed clamping block and to lock said rotation.

13. Apparatus of claim 11 wherein said fixed clamping block is journaled for rotation of said shaft and said shaft is threaded into said clamping block to firmly connect said clamping block and said fixed clamping block and to lock said rotation.

14. Apparatus of claim 10 wherein said second pivot is a dowel pin on which said clamping block is rotatable and said clamping block is rotationally locked by fasteners which are positioned on opposite sides of said dowel pin and which connect said clamping block to said fixed clamping block.

15. Constant load differential dilatometer comprising
   (a) a linear variable differential transformer having an axially movable core freely floating in an independent axially movable coil, at least one member selected from said core and coil being coupled to a pushrod adapted to abut a specimen and being independently supported for application of a constant load to said specimen, said selected member bearing a pair of straight elongated extensions positioned parallel to its path of axial movement,
   (b) adjustable support apparatus which permits long range axial movement and alignment adjustment of said selected member while rigidly restricting transverse movement thereof, said support apparatus comprisng
      (i) a pair of collars, each of which slidably engages one of said extensions, said pair of collars being held in firm alignment by a yoke,
      (ii) adjustable clamping means attached to said yoke for rotating and locking said yoke on a first plane parallel to the longitudinal axis of said selected member, thereby tilting said collars and said selected member on said first plane, and
      (iii) second adjustable clamping means attached to said adjustable clamping means for rotating and locking said yoke on a second plane parallel to said longitudinal axis and normal to said first plane, thereby tilting said collars and said selected member on said second plane, and (c) means for varying the force applied to said specimen by said abutting pushrod.

16. Dilatometer of claim 15 wherein said selected member is the core of a linear variable differential transformer, said extensions are round rods extending coaxially from opposite ends of said core, said collars are tubular with round orifices holding linear ball bearings and said collars are held in firm coaxial alignment by said yoke.

17. Dilatometer of claim 15 wherein said selected member is the coil of a linear variable differential transformer, each of said extensions is a round rod positioned parallel to the longitudinal axis of said coil and is spaced apart from said coil and said other extension, said collars are tubular with round orifices holding linear ball bearings and said collars are held in firm parallel alignment by said yoke.

18. Dilatometer of claim 15 wherein (a) said adjustable clamping means comprises a clamping block, a pivot held intermediate said yoke and said clamping block, said yoke being lockably rotatable on a plane parallel to the longitudinal axis of said selected member, and means for locking said yoke to said clamping block and (b) said second adjustable clamping means comprises a fixed clamping block, a second pivot held intermediate said clamping block and said fixed clamping block, said clamping block being lockably rotatable on a second plane that is parallel to said longitudinal axis and normal to the plane of rotation of said yoke, and means for locking said clamping block to said fixed clamping block.

19. Dilatometer of claim 18 wherein (a) said adjustable clamping means comprises
   (i) a clamping block and
   (ii) a first shaft extending between said yoke and said clamping block,
   said first shaft being positioned perpendicular to the longitudinal axis of said selected member, said yoke being rotatable on said first shaft on a first plane parallel to said longitudinal axis and said first shaft being a threaded fastener for firmly connecting said yoke to said clamping block and for locking said rotation, and (b) said second adjustable clamping means comprises
   (iii) a fixed clamping block and
   (iv) a second shaft extending between said clamping block and said fixed clamping block,
   said second shaft being positioned perpendicular to the longitudinal axis of said selected member and said first shaft, said clamping block being rotatable on said second shaft on a second plane parallel to said longitudinal axis and perpendicular to said first plane and said second shaft being a threaded fastener for firmly connecting said clamping block to said fixed clamping block and for locking said rotation.

20. Dilatometer of claim 18 wherein (a) said adjustable clamping means comprises
   (i) a clamping block,
   (ii) a first dowel pin positioned between said yoke and said clamping block,
   (iii) a first pair of threaded fasteners connecting said yoke to said clamping block on opposite sides of said first dowel pin,
   said first dowel pin being positioned perpendicular to the longitudinal axis of said selected member and being retained in shallow mating depressions in said yoke and said clamping block, said yoke being rotatable on said first dowel pin on a first plane parallel to said longitudinal axis and the rotation of said yoke being lockable by said first pair of threaded fasteners, and (b) said second adjustable clamping means comprises
   (iv) a fixed clamping block,
   (v) a second dowel pin positioned between said clamping block and said fixed clamping block and
   (vi) a second pair of threaded fasteners connecting said clamping block to said fixed clamping block on opposite sides of said second dowel pin,
   said second dowel pin being positioned perpendicular to the longitudinal axis of said selected member and said first dowel pin and being retained in shallow mating depressions in said clamping block and said fixed clamping block, said clamping block being rotatable on said second dowel pin on a second plane parallel to said longitudinal axis and perpendicular to said first plane and the rotation of said clamping block being lockable by said second pair of threaded fasteners.

* * * * *